United States Patent [19]

Wright

[11] Patent Number: 5,043,478

[45] Date of Patent: Aug. 27, 1991

[54] PROCESS FOR THE PREPARATION OF FLUORINATE AROMATIC DIAMINE

[75] Inventor: William E. Wright, Baton Rouge, La.

[73] Assignee: Ethyl Corporation, Richmond, Va.

[21] Appl. No.: 340,510

[22] Filed: Apr. 18, 1989

[51] Int. Cl.$^5$ .................. C07C 217/90; C07C 217/92
[52] U.S. Cl. ..................................... 564/315; 568/586
[58] Field of Search ........................ 564/315; 368/586

[56] References Cited

U.S. PATENT DOCUMENTS

| | | | |
|---|---|---|---|
| 2,544,076 | 3/1951 | Fourneau | 564/354 X |
| 2,935,439 | 5/1960 | Wright et al. | 564/354 X |
| 3,542,735 | 11/1970 | Lynch | 260/47 |
| 4,203,922 | 5/1980 | Jones et al. | 260/570 |
| 4,521,623 | 6/1985 | Jones et al. | 564/315 |
| 4,808,754 | 2/1989 | Guggenheim et al. | 569/315 X |

Primary Examiner—Richard L. Raymond
Attorney, Agent, or Firm—Richard J. Hammond

[57] ABSTRACT

An improved process for the preparation of certain fluorinated aromatic diamines is disclosed. The stepwise addition of an alkali metal hydroxide to the starting material produces increased yields of higher purity diamine product.

2 Claims, 1 Drawing Sheet

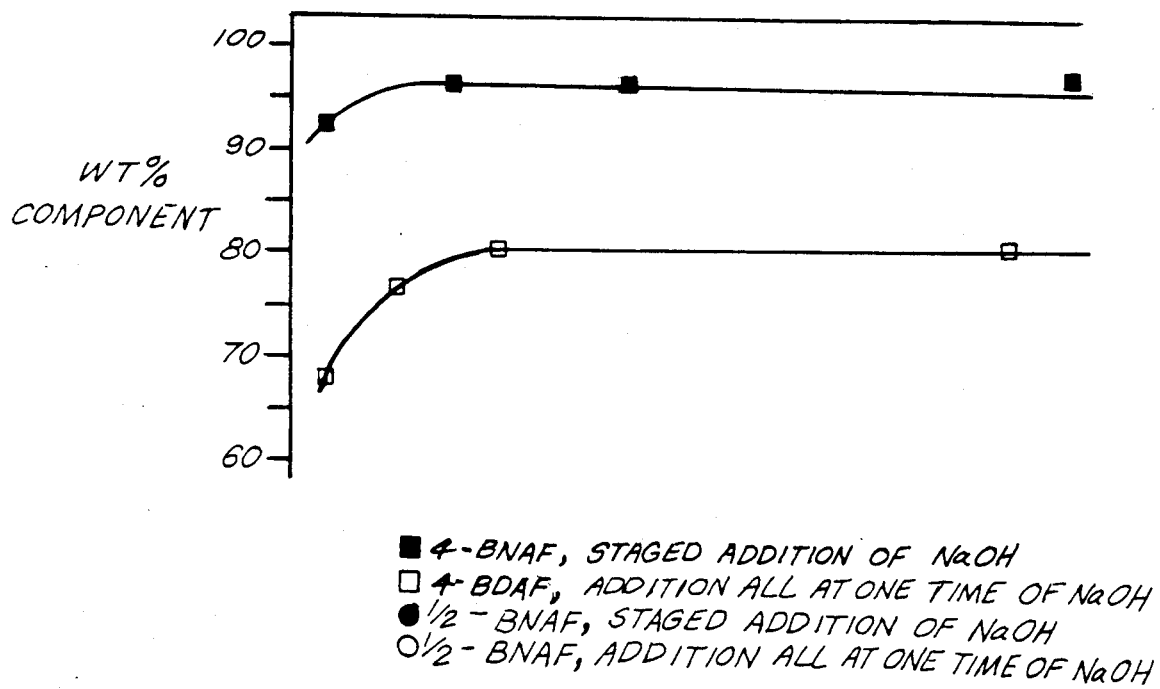
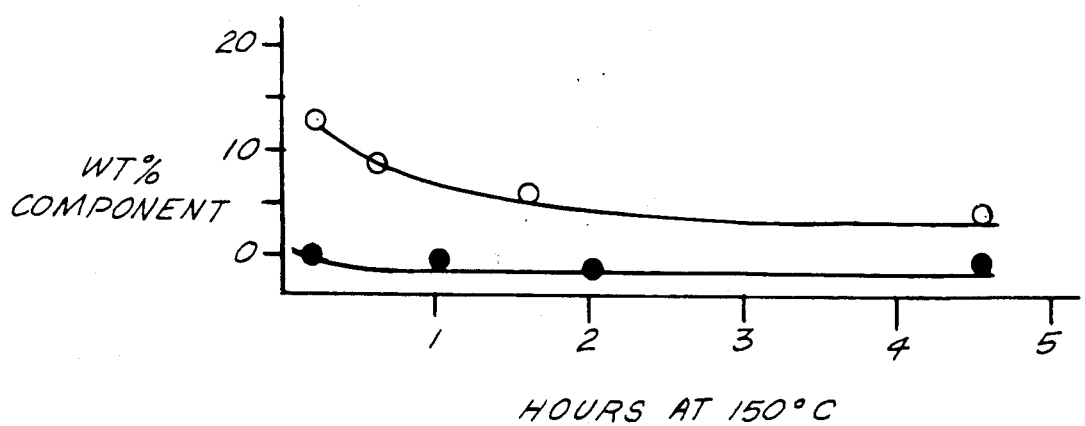

PROCESS FOR THE PREPARATION OF FLUORINATE AROMATIC DIAMINE

BACKGROUND OF THE INVENTION

In U.S. Pat. No. 3,528,950 a fully imidized prepolymer having reactive end groups is disclosed. In this disclosure, the water of imidization is removed before final cure of the prepolymer during fabrication of the polyimide product, thus solving the prior problem of void formation from water vaporization. However, solvent solubility was not as desirable as many fabricators would prefer.

Subsequently, U.S. Pat. No. 3,812,159 taught that a dianhydride monomer containing a phenoxyphenyl sulfone linkage could be used in the process taught by U.S. Pat. No. 3,528,950, and which would provide polyimides with improved solubility. The characteristics and synthesis methods for these polyimides are taught in U.S. Pat. No. 3,699,073.

While U.S. Pat. No. 3,812,159 solves the solubility problem, the high temperature stability of the sulfone-containing polyimide is not satisfactory. U.S. Pat. No. 4,203,922 seeks to improve the chemical and thermal stability of polyimides by incorporating an fluorine-containing aromatic diamine compound into the polymeric chain while maintaining their solubility characteristics. The compound may be characterized by the following formula:

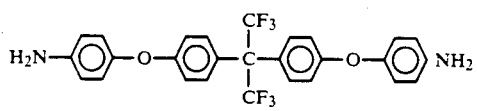

This compound is synthesized by an aromatic nucleophilic substitution of the chloro group on 4-chloronitrobenzene with a phenoxide ion.

The above reaction is initiated by reacting stoichiometric amounts of 2,2-bis(4-hydroxyphenyl)hexafluoropropane with sodium hydroxide to produce the disodium salt according to the following equation:

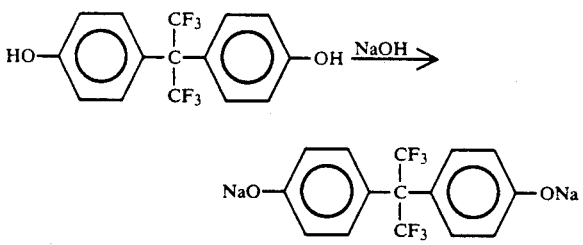

This reaction produces an intermediate compound which is sufficiently active to enter into a nucleophilic displacement reaction with the chloro-substituent on 4-chloronitrobenzene to produce 2,2-bis[4-(4-nitrophenoxy)phenyl]hexafluoropropane, as follows:

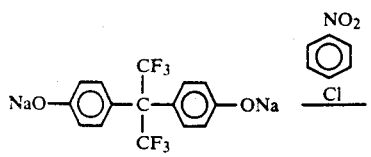

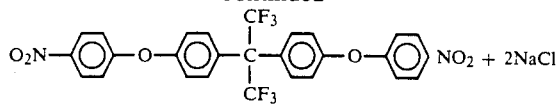

Reduction of the dinitro compound to the corresponding diamine is accomplished by reacting the compound with water in the presence of iron, stannous chloride, or reduction with hydrogen with palladium as a catalyst.

The reaction to form the sodium alkoxide is difficult to control because of the occurrence of a variety of side reactions. Sodium hydroxide typically attacks the solvent in addition to the bisphenol compound. A monosodium intermediate is also formed in the first (sodium hydroxide) step leading to:

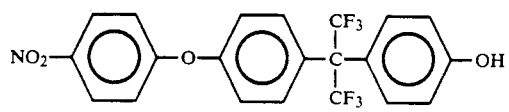

and the corresponding monoamine on hydrogenation. The end result of this myriad of competing reactions is that the yield of desired diamine is severely depressed and its purity is adversely affected.

It is an object of this invention to provide a reaction sequence where 2,2-bis[4-(4-aminophenoxy)phenyl]hexafluoropropane can be produced with a minimum of side reactions.

It is a further object of the present invention to provide a process for the preparation of 2,2-bis[4-(4-aminophenoxy)phenyl]hexafluoropropane that is of high purity.

SUMMARY OF THE INVENTION

According to the present invention, there is provided a novel process for preparing 2,2-bis[4-(4-aminophenoxy)phenyl]hexafluoropropane (termed thereafter as 4-BDAF).

The improved process involves the addition of the sodium hydroxide of step (1) to the reaction mixture in a controlled manner over a specific period of time.

DESCRIPTION OF THE DRAWINGS

FIG. 1 is a graph comparing the rates of formation of the intermediate 2-(4-hydroxyphenyl)-2-(4-nitrophenoxy)phenylhexafluoropropane (½ BNAF) and the final product 4-BDAF by the process of the invention and by the prior art process.

DETAILED DESCRIPTION OF THE PREFERRED EMBODIMENTS

Typically, a solution of 2,2-bis(4-hydroxyphenyl)hexafluoropropane in an aprotic solvent is first formed and heated. An aqueous solution of sodium hydroxide is then added over a period of from about 15 minutes to about 4 hours, preferably 20 minutes to 3 hours, most preferably 30 minutes to 2 hours. Water evolving from the reaction is collected until the quantity obtained indicates substantially complete reaction.

The aprotic solvents useful in the above step (1) reaction include:
N,N-dimethylformamide
N,N-dimethylacetamide
N-methylpyrrolidone
dimethylsulfoxide tetrahydrofuran
diethylene glycol dimethyl ether
triethylene glycol dimethyl ether
dimethoxyethane, and the like Generally, other solvents may be present in appropriate proportions and may include:
acetone
methylethylketone
toluene
xylene
1,2,3,4-tetramethylbenzene
1,2,3,5-tetramethylbenzene
1,2-diethylbenzene
1,3-diethylbenzene
1,4-diethylbenzene
3,5-diethyltoluene
n-butylbenzene
3-proxyltoluene
4-propyltoluene
tetrahydronaphthalene
and the like, including mixtures of two or more such solvents. If any of these materials are low melting solids at room temperature, they should be mixed with a suitable liquid solvent such that the resultant mixture is a liquid at somewhat below room temperature.

Needless to say, the reactants and solvent(s) used in forming the compositions of this invention should have sufficiently high purities to satisfy the requirement that the BDAF product be of high purity. Thus the solids are preferably recrystallized from highly pure solvents and the liquids are preferably purified by use of distillation or other purification techniques.

The following examples illustrate the preferred method of synthesizing BDAF according to this invention.

EXAMPLE 1

1) A one liter round bottomed flask was fitted with mechanical stirrer, thermometer, nitrogen inlet, Dean-Stark trap and reflux condenser. To this was charged 2,2-bis[4-hydroxyphenyl]hexafluoropropane (100.8 g; 0.30 mole); dimethylacetamide (281.2 g), and toluene (131 g). After stirring for a few minutes the reaction mass was brought to reflux and a 50% aqueous solution of sodium hydroxide (52.8 g; 0.66 mole) was slowly added (about 5 g every 10 minutes) over a period of 1.9 hours. 44 grams of "water" collected in the Dean-Stark trap as the temperature of the reaction mixture rose from 107° to 135° C. over a period of three and one half hours. The reaction mass was allowed to cool and a 23 gram portion of this was set aside for future use. The remainder was stirred and heated to remove toluene by atmospheric distillation. 124 grams of toluene was collected over about a 1 hour period and then the reaction mass was allowed to cool to 90° C.

2) Parachlorinitrobenzene (94.6 g; 0.60 mole) was added, causing the temperature to fall to about 60° C. Heating and stirring were resumed. The reaction mixture was maintained at 150° C. for four hours. Samples that were removed from the reaction mass during this four hour period were extracted (toluene; dilute HCl; water) and analyzed by GLC. The results are summarized in FIG. 1.

The reaction mixture was cooled to 50 and then slowly stirred into a solution of 182 grams of methanol in 680 grams of cold tap water. After cooling the resulting slurry to 30° C., the granular precipitate of crude 4-BNAF was collected by filtration. It was washed with 20% aqueous methanol (1×172 g and 1×86 g) and dried at 65° C. overnight to yield crude 2,2-bis[4-(4-nitrophenoxy)phenyl]hexafluoropropane (4-BNAF). Analyses of this product showed that the major impurities were 1-(4-hydroxyphenyl)-2-(4-nitrophenoxy)phenyl-hexafluoropropane and p-chloronitrobenzene.

100 grams of the crude 2,2-bis[4-(4-nitrophenoxy)-phenyl]hexafluoropropane prepared above were recrystallized from 100 grams ethylacetate and 200 grams of methanol. After washing with methanol (3×30 grams) and oven-drying at 60°60 C. for two hours, the pure material (88% yield) was collected. GLC analysis showed that its purity was 96.7% and that the major impurity was the 4-hydroxy 4-(nitrophenoxy)phenyl compound.

3) 50 grams of the pure nitro compound were dissolved in 150 g ethylacetate and hydrogenated at room temperature over a period of about two hours at 40 psig hydrogen pressure 1.2 grams of 5% Pd-on-charcoal catalyst were used.

After filtering off the catalyst, the filtrate was evaporated by gently blowing with nitrogen at 70° C. until the solution was reduced. After cooling to 28° C., 37 grams of hexane were added with vigorous stirring. The thick cream colored slurry was filtered and the precipitate washed with 75 mL hexane. After drying in air, 4-BDAF was collected in 83% yield. GLC analysis showed that its purity was 99.8%, with 2-(4-hydroxyphenyl)-2-(4-aminophenoxy)phenylhexafluoropropane (½-BDAF) and BDNAF as the major impurities.

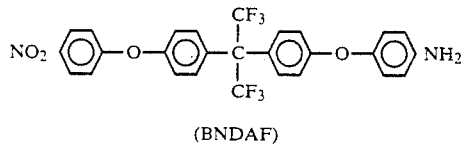

(BNDAF)

EXAMPLE 2

The procedure of Example 1 was repeated except that the addition of the aqueous sodium hydroxide was carried out over a 30 minute period. The yield of purified 4-BNAF (step 2) was 84% of theory, with a purity of 99.7%.

Hydrogenation of the material prepared above in the manner shown in Example 1, step 3, provided 4-BDAF in yield of 82% of theory. This material was 99.9% pure Examples 3 and 4 are carried out in the same manner as Example 1 except the addition times are 2 hours and 1 hour respectively. The results are depicted in FIG. 1.

COMPARATIVE EXAMPLE

The procedure of Example 1 was repeated except that the prior art method of complete addition of the aqueous sodium hydroxide at the start of the reaction was used in step 1. The yield of purified 4-BNAF (step 2) was 83% of theory having a purity of 96.6%.

The hydrogenation procedure of step 3 was carried out on the above prepared 4-BNAF resulting in 4-BDAF in a 67% yield of 98.7% purity.

The other Comparative Example was carried out except that the heating of step 1 was carried out over the period shown in Examples 2, 3 and 4, i.e., 30 minutes, 2 hours and 1 hour respectively. The results are depicted in FIG. 1.

Referring now to FIG. 1, the lower most curves illustrate the formation of the undesirable intermediate 2-(4-hydroxyphenyl)-2-(4-nitrophenoxy)phenylhexafluoropropane (½ BNAF) which is the most serious contributor to the impurity of the required intermediate 2,2-bis[4-(4-nitrophenoxy)phenyl]hexafluoropropane. The solid circle curve clearly illustrates that the staged addition of the alkali hydroxide dramatically diminishes the amount of ½ BNAF formed in this reaction.

The significance of the effect of diminishing the amount of impurity, ½ BNAF, is seen in the upper curves.

I claim:

1. In a process for preparing an aromatic diamine of the formula

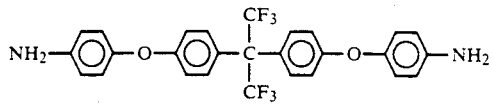

by (1) first forming the di(alkali metal) salt of 2,2-bis(4-hydroxyphenyl)hexafluoropropane by reacting 2,2-bis(4-hydroxyphenyl)hexafluoropropane with an alkali metal hydroxide; (2) treating said salt with a nitrobenzene substituted in the para position with an appropriate leaving group to form 2,2-bis[4-(4-nitrophenoxy)phenyl]hexafluoropropane; and (3) reducing the nitro compound produced in step (2) to form the aromatic diamine, the improvement comprising adding the alkali metal hydroxide of step (1) over a period of time from about 0.5 to about 1.9 hours.

2. The process of claim 1 wherein said alkali metal hydroxide is sodium hydroxide.

* * * * *